United States Patent [19]

Gouilloud et al.

[11] Patent Number: 4,628,725
[45] Date of Patent: Dec. 16, 1986

[54] APPARATUS AND METHOD FOR ANALYZING A FLUID THAT INCLUDES A LIQUID PHASE, CONTAINED IN A TUBULAR CONDUIT

[75] Inventors: Michel M. A. Gouilloud, Ridgefield; Thomas J. Plona, New Milford, both of Conn.

[73] Assignee: Schlumberger Technology Corporation, New York, N.Y.

[21] Appl. No.: 717,403

[22] Filed: Mar. 29, 1985

[51] Int. Cl.⁴ ............................................. G01N 29/02
[52] U.S. Cl. ....................................... 73/19; 73/861.27
[58] Field of Search ................... 73/19, 861.25, 861.26, 73/861.27, 861.29, 153

[56] References Cited

U.S. PATENT DOCUMENTS

| | | | |
|---|---|---|---|
| 1,881,543 | 10/1932 | Hartig et al. | 73/861.27 |
| 2,151,203 | 3/1939 | Hartig | 73/861.27 |
| 2,274,262 | 2/1942 | Wolff | 73/861.27 |
| 2,534,712 | 12/1950 | Gray | 73/861.27 |
| 2,573,390 | 10/1951 | Blanchard | 73/19 |
| 2,991,650 | 7/1961 | Katzenstein et al. | 73/861.28 |
| 3,127,950 | 4/1964 | Itria | 367/26 |
| 3,130,808 | 4/1964 | Walker, Jr. et al. | 73/155 |
| 3,283,562 | 11/1966 | Heisig et al. | 73/19 |
| 4,003,252 | 1/1977 | Dewath | 73/861.27 |
| 4,130,010 | 12/1978 | Wonn | 73/19 |
| 4,131,875 | 12/1978 | Ingram | 73/152 |
| 4,164,865 | 8/1979 | Hall et al. | 73/861.28 |
| 4,236,406 | 12/1980 | Reed et al. | 73/61.1 R |
| 4,432,077 | 2/1984 | Alhilali et al. | 367/31 |
| 4,445,389 | 5/1984 | Potzick et al. | 73/861.27 |
| 4,452,077 | 6/1984 | Siegfried, II | 73/155 |
| 4,490,609 | 12/1984 | Chevalier | 250/269 |

FOREIGN PATENT DOCUMENTS 0131351 1/1985 European Pat. Off. .

OTHER PUBLICATIONS

K. A. Sage et al., "Multipole Resonances in Sound Scattering from Gas Bubbles in a Liquid", *J. Acous. Soc. Am.*, vol. 65, No. 6, pp. 1413–1422, Jun. 1979.
Stoneley, R., "Elastic Waves at the Surface of Separation of Two Solids", *Proc. Roy. Soc., Series A*, vol. 106, 1924, pp. 416–428.
Schoenberg et al., "Space-Time Dependence of Acoustic Waves in a Borehole", *Journal of the Acoustical Society of America*, vol. 70, No. 5, Nov. 1981, pp. 1496–1507.
van der Hijden et al., "Acoustic Modes in a Borehole with a Concentric Fluid-Filled Elastic Tube", *Proc. of 54th Annual Mtg. of SEG*, Dec. 1984: Borehole Geophysics I, pp. 7–9.
Kimball, C. V. et al., "Semblance Processing of Borehole Acoustic Array Data", *Geophysics*, vol. 49, No. 3, Mar. 1984, pp. 274–281.

*Primary Examiner*—Stephen A. Kreitman
*Attorney, Agent, or Firm*—Stephen L. Borst; David G. Coker; David H. Carroll

[57] ABSTRACT

Apparatus and methods for the flow analysis of multiphase fluids including a liquid phase in a tubular conduit use Stoneley waves by exciting and detecting sonic wave energy in the tubular conduit. Information about the Stoneley mode component is obtained in one approach by using techniques that excite only the Stoneley mode together with certain other well behaved wave types, and then compensating for the latter. Alternatively the Stoneley arrival is specifically identified in the detected waveforms. Embodiments are described for: determining the flow rate of a liquid; detecting the presence or absence of gas in a liquid; determining the composition by volume of the dispersed phases in a multiphase fluid; determining the size distribution of bubbles in a multiphase fluid; and determining the velocity of slugs in a multiphase fluid.

26 Claims, 19 Drawing Figures

APPARATUS AND METHOD FOR ANALYZING A FLUID THAT INCLUDES A LIQUID PHASE, CONTAINED IN A TUBULAR CONDUIT

BACKGROUND OF THE INVENTION

The present invention relates to a method and apparatus for analyzing a fluid that includes at least one liquid phase, contained in a tubular conduit; and more particularly to a method and apparatus for analyzing a fluid that includes a liquid phase, contained in a tubular conduit, using the sonic Stoneley wave.

Many industrial activities involve an analysis of fluids that include at least one liquid phase, contained in a tubular conduit. In one such activity, viz. providing drilling and production services to the oil industry, one may be particularly interested in providing an early detection of gas intruding in the mud during drilling, or a detection of gas presence and bubble distribution in drill stem testing, or in obtaining production or injection profiles, or in analyzing flowing slurries or mud cuttings. Other activities include measuring the characteristics of flowing fluids that include a liquid phase, involved in industrial processes and in distribution systems.

Many different techniques have been proposed to measure flow characteristics of fluids, i.e. liquids, gases, and combinations thereof (multiphase fluid), contained in tubular conduits. For example, some known techniques are based on sensing and correlating local pressure fluctuations, and on sensing the pressure field set up by a venturi or vortex element. A number of other well known techniques are based on the propagation of sonic or ultrasonic energy in a flowing fluid.

Examples of techniques for determining fluid velocity that involve the use of sonic energy propagating in the fluid are disclosed in the following U.S. Pat. Nos. 1,881,543, issued Oct. 11, 1932 to Hartig et al.; 2,151,203, issued Mar. 21, 1939 to Hartig; 2,274,262, issued Feb. 24, 1942 to Wolff; 2,534,712, issued Dec. 19, 1950 to Gray; and 4,003,252, issued Jan. 18, 1977 to Dewath. The apparatus disclosed in the Hartig et al. U.S. Pat. No. 1,881,543 uses sound tubes inserted through the tube into the fluid flow and measures fluid velocity with a reflection-compensated continuous wave, or "CW" measurement technique. The apparatus disclosed in the Hartig U.S. Pat. No. 2,151,203 uses ports along a tube and measures fluid velocity with a travel time technique. The apparatus disclosed in the Wolff patent uses ports along a tube and measures air velocity with a CW technique. The apparatus disclosed in the Gray patent introduces sonic pulses into an unconfined air stream and determines air velocity with a travel time technique. The apparatus disclosed in the Dewath patent uses transducers recessed in the acoustically damping liner of a tube, which achieves a fluid flow conduit substantially devoid of protuberances and cavities. A CW technique is used to determine fluid velocity.

Another nonintrusive instrument that overcomes some of the disadvantages of the Dewath apparatus is disclosed in U.S. Pat. No. 4,445,389, issued May 1, 1984 to Potzick et al. An acoustic technique is discussed which involves the use of wavelengths longer than the cutoff wavelength of the conduit, such that when the acoustic waves reach the receivers, the cutoff spatial modes will have decayed nearly to zero and only the fundamental waves will be present. A CW technique is used to determine fluid velocity and sound velocity.

Most of these techniques are said to be applicable to fluids generally, including liquids such as oil and water. yet, none of these techniques has been adapted to oilfield service applications, where the fluid is a liquid or a multiphase fluid including a liquid phase. The techniques that rely on extensive use of damping materials are impractical for most environments encountered in oilfield services, while the other techniques either fail or are not reliable when used to investigate a liquid or multiphase fluid.

The technique disclosed in U.S. Pat. No. 4,236,406, issued Dec. 2, 1980 to Reed et al., involves the use of ultrasonic energy directed through the fluid being investigated, for determining fluid sound velocity. The technique is said to be capable of metering water content in an oil-water system by the determining sonic velocities in the flowing oil-water mixture. Other ultrasonic techniques are disclosed in U.S. Pat. No. 2,991,650, issued July 11, 1961 to Katzenstein et al. Various propagation paths, including one approximately along the longitudinal axis of a portion of a pipe, are illustrated and described.

Ultrasonic techniques have been adapted for use in oilfield servies, as disclosed in U.S. Pat. No. 4,452,077, issued June 5, 1984 to Siegfried; and U.S. Pat. No. 3,130,808, issued Apr. 28, 1965 to Walker, Jr. et al. These techniques share a disadvantage with the nonborehole ultrasonic techniques, viz. they sample only a limited region of the fluid under investigation. Hence, they are not advantageous in applications for which a measurement independent of flow profile is desired. The technique disclosed in the Siegfried patent further is disadvantageous in being adversely affected by tool eccentricity, irregularities in the well casing, and particulates and gas phases in the borehole liquid.

SUMMARY OF THE INVENTION

An object of the present invention is to measure the velocity of the Stoneley mode in a fluid that includes a liquid phase, contained in a tubular conduit.

Another object of the present invention is to measure the velocity of a liquid flowing in a tubular conduit, using the Stoneley mode.

Another object of the present invention is to detect the presence of a gas phase in a liquid contained in a tubular conduit, using the Stoneley mode.

Yet another object of the present invention is to determine the composition of dispersed phases in a multiphase fluid contained in a tubular conduit, using the Stoneley mode.

A further object of the present invention is to determine size distribution of bubbles in a multiphase fluid contained in a tubular conduit, using the Stoneley mode.

A further object of the present invention is to determine the velocity of slugs in a multiphase fluid contained in a tubular conduit, using the Stoneley mode.

These and other objects are obtained in the present invention, a method and apparatus for analyzing a fluid that includes a liquid phase, contained in a tubular conduit. In analyzing such fluids, one is interested in such characteristics as the flow rate of a liquid, the presence or absence of gas in a liquid, the composition by volume of the dispersed phases in a multiphase fluid, the size distribution of bubbles in a multiphase fluid, and the velocity of slugs in a multiphase fluid. These and other characteristics are measured in the present invention using a Stoneley wave. Sonic wave energy is excited and detected in the tubular conduit. Certain information about the Stoneley mode component is obtained either by techniques that excite only the Stoneley mode and certain well behaved wave types, and compensate for the latter; or that specifically identify the Stoneley arrival in the detected waveforms. In one embodiment, the flow rate of a liquid is determined from the Stoneley velocity. In another embodiment, the presence or absence of gas in a liquid is detected from either the Stoneley velocity or amplitude. In another embodiment, the composition by volume of the dispersed phases in a multiphase fluid is determined from the Stoneley velocity. In another embodiment, the size distribution of bubbles in a multiphase fluid is determined from a frequency spectrum of the Stoneley amplitude. In another embodiment, the velocity of slugs in a multiphase fluid is determined from a doppler effect experienced by the Stoneley wave.

BRIEF DESCRIPTION OF THE DRAWINGS

In the drawings, where like reference characters indicate like parts.

DETAILED DESCRIPTION OF THE PREFERRED EMBODIMENTS

The Stoneley wave has been found to be advantageous for use in determining certain characteristics of a fluid flowing in a tubular conduit. These characteristics include fluid velocity, fluid composition where the fluid contains dispersed phases, bubble distribution where the fluid contains bubbles, and slug velocity. As used herein, the term "tubular" means an enlongated closed channel preferably but not necessarily cylindrical in shape. The term "Stoneley wave" refers to a type of guided wave reported by R. Stoneley in Stoneley, R., Proc. Roy. Soc., Series A, Vol. 106, 1924, p 416 ff.

The Stoneley mode also is found in the geometry of a stiff tubular conduit, suitable for transporting fluid. The velocity of the Stoneley wave is always less than, although generally close to, fluid sound velocity. Stoneley wave energy is asymptotically confined to the fluid with increasing tube stiffness. Attenuation of the Stoneley wave along the length of the tubular conduit is very small where the tubular conduit is filled with a single phase fluid; in theory, the Stoneley wave does not attenuate at all. Where the wavelength of the sonic energy in the fluid is comparable with the diameter of the tubular conduit, the Stoneley wave does not experience much decay across the tubular conduit. At even lower fequencies where the Stoneley wave may be referred to as a tube wave, the Stoneley field strength is practically flat across the tubular conduit.

Acoustic propagation in the tubular conduit of a fluid analyzer can be extremely complex in oilfield service applications where the fluid is a liquid. This complexity is explained herein with reference to two studies of wideband acoustic propagation in an oil well, one by Schoenberg et al., Space-time Dependence of Acoustic Waves in a Borehole, Journal of the Acoustical Society of America, Vol. 70, No. 5, November 1981, pp. 1496–1507; and the other by van der Hijden et al., Acoustic Modes in a Borehole with a Concentric Fluid-Filled Elastic Tube, Proceedings of the 54th Annual Meeting of the SEG, December 2-6, 1984; Borehole Geophysics I—Full Wave Sonic Logging, 1984, pp. 7-9. The Schoenberg et al. article shows that the complexity is due to the presence of headwaves, trapped fluid modes, and surface waves. The van der Hijden article adds that where a logging tool is present in the borehole, new modes such as the extensional and tube modes further complicate the acoustic propagation. This complexity may not be present in fluid analyzers used in other than oilfield service applications, where the fluid is a gas, or where damping materials are suitably used in the design of the fluid analyzer.

Moreover, certain oilfield service applications require that the fluid analyzer operate where dispersed phases, bubbles, and/or slugs are present. In these circumstances, acoustic waves may not be strongly coupled between the fluid and the transducers, and other well coupled waves may interfere with detection of the Stoneley wave.

Figure 1:
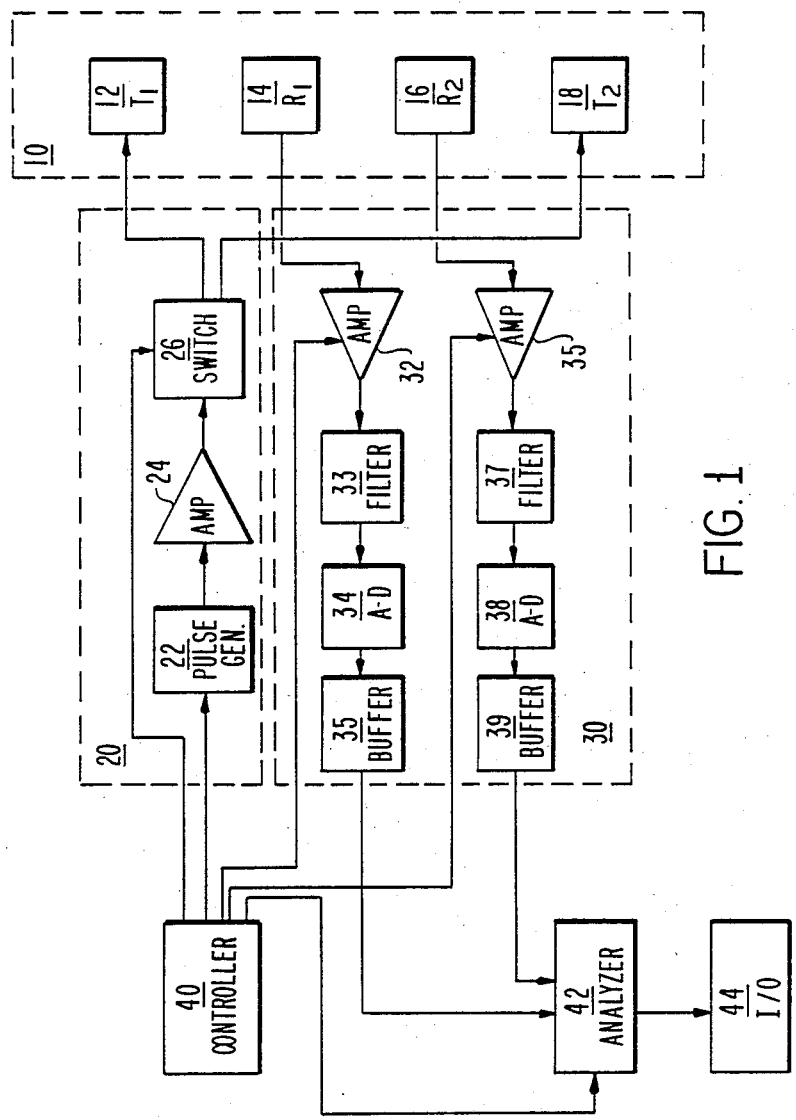
FIG. 1 is a schematic diagram which includes a schematic illustration of a general embodiment of the present invention.

A preferred basic embodiment of the fluid analyzer is illustrated in FIG. 1. The apparatus of FIG. 1 is digital, although analog equivalents are contemplated as well. The apparatus of FIG. 1 operates in the pulse mode. Shown in FIG. 1 are a sensor section 10, a transmitter section 20, a receiver section 30, a controller 40, an analyzer 42, and an input-output device 44.

The sensor section 10 comprises sonic transducers 12, 14, 16 and 18. A cylindrical, relatively broadband transducer is preferred. A cylindrical shape matching the contour of the tubular conduit is preferred, as this shape is likely to couple the greatest energy into the fluid flowing within the tubular conduit. A broadband response is preferred, as pulse techniques have been found to be particularly suitable for use in oilfield service applications. Suitable transducer materials include ceramics and magnetostrictive materials.

The four transducers 12, 14, 16 and 18 are spaced in an array longitudinally in the tubular conduit, preferably although not necessarily with their respective axes coincident with one another and with the axis of the tubular conduit. Transducers 12 and 18 are operated as transmitters, hence are referenced herein by T1 and T2. Transducers 14 and 16 are operated as receivers, hence are referenced herein by R1 and R2. It will be appreciated that the simplest array comprises a single transmitter transducer spaced apart from a single receiver transducer. In practice, however, processing is best performed on waveforms provided by at least two spaced apart receivers. A second transmitter is provided for measuring Stoneley wave velocity over the same receiver interval but in the opposite direction.

The number of receivers to be included in the transducer array depends on the frequency of operation and signal processing technique applied. Operation at a suitably low frequency, as explained below, eliminates the higher order modes, making feasible the use of very simple gating or threshold techniques to eliminate the remaining undesirable arrivals, a reduction in the number of receivers to preferably two or fewer, and the use of very simple and fast signal processing techniques to measure Stoneley wave travel time. Operation at higher frequencies will excite the higher order modes, requiring the use of many receivers in the array and the use of complicated and in some instances computationally intensive signal processing techniques to identify the Stoneley arrival and determine its velocity. Such techniques include, for example, those taught in U.S. Pat. No. 4,131,875, issued Dec. 26, 1978 to Ingram, and the technique taught in commonly assigned U.S. application Ser. No. 593,932, filed Mar. 27, 1984 in the name of Kimball et al. For the latter, see also Kimball, C. V. and Marzetta, T. L., Semblance Processing of Borehole Acoustic Array Data, Geophysics, Vol. 49, No. 3, March 1984, PP. 274–81.

Transmitter section 20 comprises a pulse generator 22, the output of which is amplified by amplifier 24 and provided to a selected transducer T1 or T2 via switch 26.

Receiver section 30 comprises two identical digital channels, each including an amplifier for amplifying a detected signal, a filter for eliminating undesired frequencies, an analog-digital converter for digitizing the amplified detected signal, and a buffer for storing the digitized waveform. These elements are, respectively, 32, 33, 34 and 35 for one of the channels, and 36, 37, 38 and 39 for the other channel.

Controller 40 controls the functions of switch 26 and amplifiers 32 and 36, in a manner discussed in detail below. Analyzer 42 is responsive to information in the detected acoustic energy for determining the measurement of interest, as described in detail below.

Figure 4:
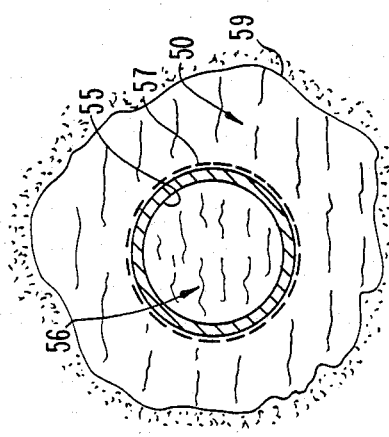
FIGS. 2, 3 and 4 are sketches of the geometry of three illustrative embodiments of the present invention.
Figure 3:
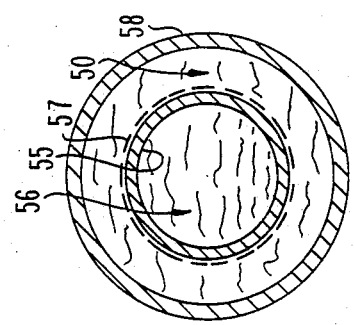
Figure 2:
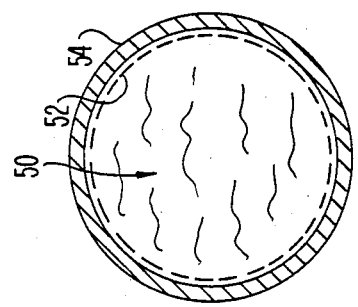

Certain parameters of the fluid analyzer of the present invention, such as sensor configuration, bandwidth and center frequency, are evaluated based on the application and the environment in which the fluid analyzer will operate. As will be apparent in the preferred embodiments introduced below, three cases are of particular interest. The transducers of sensor section 10 may couple to the fluid to be analyzed from the inside of the tubular conduit, as shown in FIG. 2 where a subject fluid is indicated generally at 50, an annular transducer is indicated at 52, and a pipe is indicated at 54. Alternatively, the transducers of sensor 10 may couple to the fluid to be analyzed from a support member disposed in the fluid, within the tubular conduit, as shown in FIGS. 3 and 4 where a subject fluid is indicated generally at 50 and a logging sonde is represented as a tubular member 55 containing a fluid 56 and supporting an annular transducer 57. The tubular conduit may be, for example, production tubing 58 (FIG. 3) or, in a special case, an earth formation 59 traversed by a borehole (FIG. 4).

Figure 5:
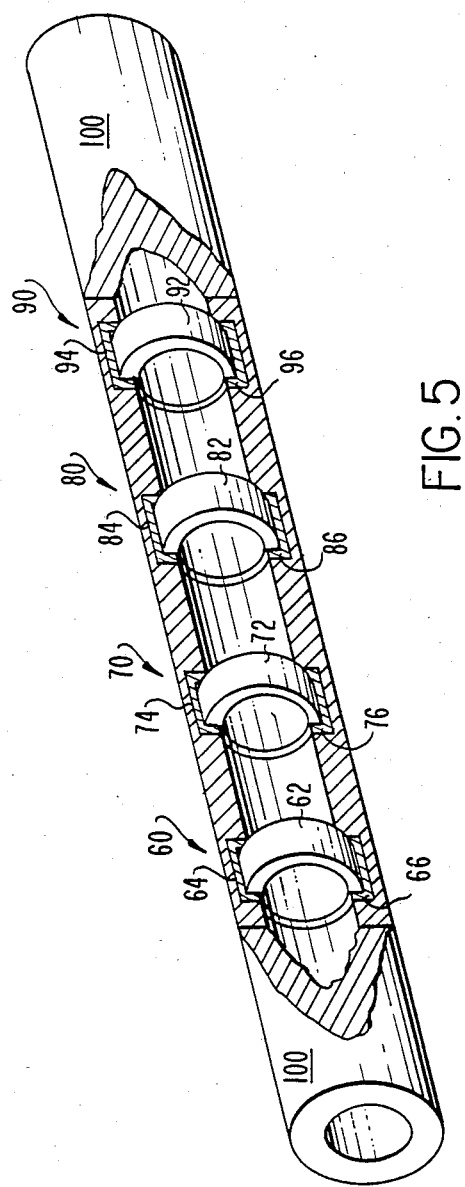
FIGS. 5, 6 and 7 are combined plan and cross sectional views of three embodiments of the present invention.

A preferred embodiment of a fluid analyzer of the FIG. 2 type, suitable for use in, for example, a drill stem testing sonde or in a production pipeline, or in applications such as industrial process facilities and fluid distribution or discharge systems, is illustrated in FIG. 5. Four annular sonic transducers 60, 70, 80 and 90, preferably of the magnetostrictive type, are mounted inside of a steel tube 100. Each transducer is set in an annular cavity, and backed by a suitable acoustic damping material if desired. For example, transducer 60 comprises an annular active element 62, made of a magnetostrictive material, set in an annular cavity 64 and backed by acoustic damping material 66. Magnetostrictive transducers are well known generally, so that design features are not described in detail herein. Transducers 70, 80 and 90 are similarly constructed. Respective electrical conductors (not shown) connect the elements 62, 72, 82 and 92 to a suitable electronic circuit. The inside surface of the tube preferably is of a uniform cross section and is smooth, which avoids the introduction of contrasting sonic impedances which cause undesired reflections of the Stoneley wave. Moreover, the end segments of tube 100 preferably are long so as to preserve a constant cross section in the vicinity of the flow analyzer elements.

Figure 6:
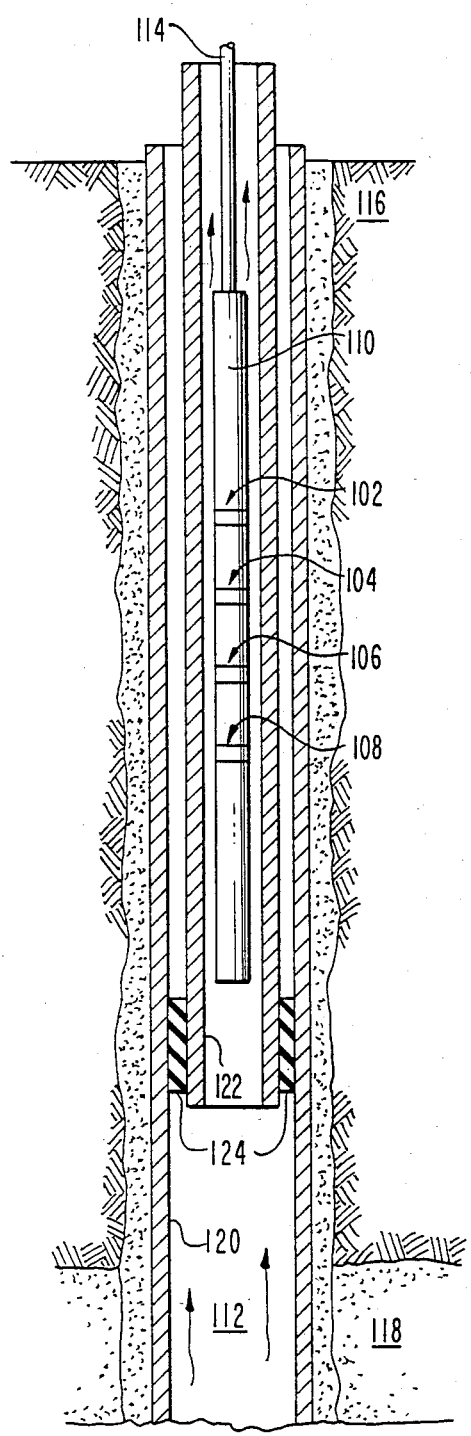

A preferred embodiment of a fluid analyzer of the FIG. 3 type, advantageous for use in production logging, is illustrated in FIG. 6. Four annular sonic transducers 102, 104, 106 and 108 are mounted on a mandrel sonde body 110, suspended in a borehole 112 on an armored multiconductor cable 114 from surface equipment (not shown). Each of the transducers 102, 104, 106 and 108 preferably is of the magnetostrictive type. Magnetostrictive transducers are well known generally, so that design features are not described in detail herein. Surface equipment, generally well known in the art, includes a drum and winch mechanism, a depth measuring wheel, and a general purpose computer for signal processing and control functions. The borehole traverses earth formations 116 and 118, the latter being a permeable formation which is produced through perforations (not shown) through casing 120. Production casing 122 is set within casing 120 and sealed with production packer 124. The inside surface of production casing 122 preferably is of a uniform cross section and is smooth, to avoid the introduction of contrasting sonic impedances which cause undesired reflections of the Stoneley wave. Relative minor discontinuities such as found in the joints are tolerable. Moreover, the mandrel 110 preferably is extended longitudinally at its ends, so as to preserve a constant cross section in the vicinity of the fluid analyzer elements.

Figure 7:
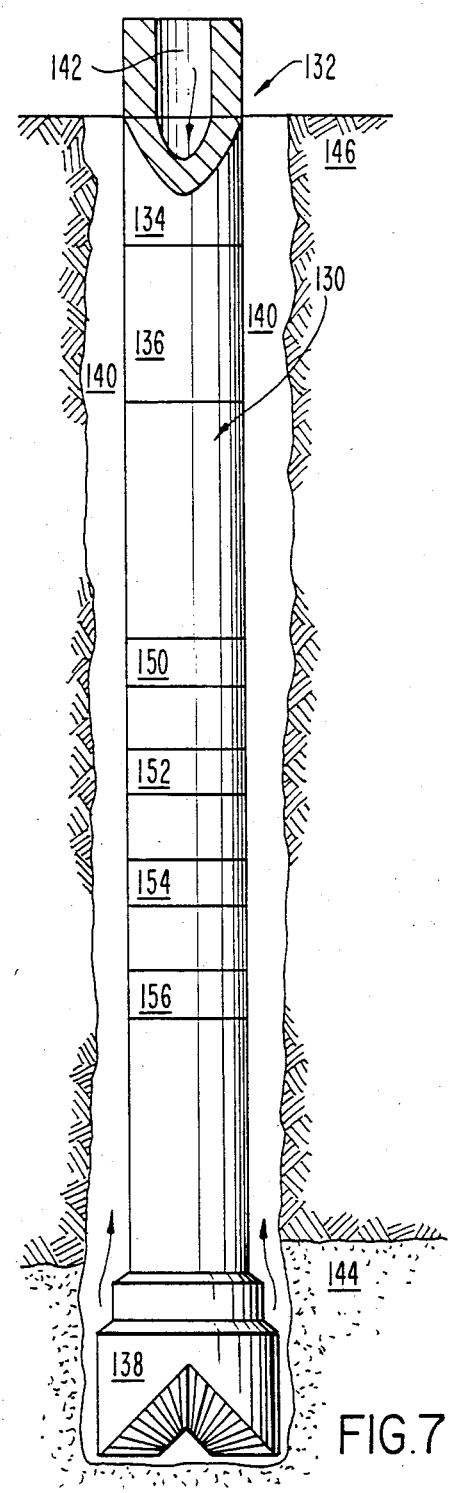

A preferred embodiment of the fluid analyzer of the FIG. 4 type, advantageous for use in measurement while drilling oilfield service operations, is illustrated in FIG. 7. The tool, indicated generally at 130, is shown coupled in a typical drill string 132 comprising drill pipe sections 134 and 136, and a rotary drill bit 138. As the drill string 132 is rotated by a suitable drilling rig (not shown) at the surface, a suitable drilling fluid is circulated about the rotary bit 138 and through the borehole 140, to cool the bit, stabilize the well, and remove earth borings from the well. This fluid, commonly a liquid slurry known as "mud," is pumped from a surface reservoir through the interior of the drill string (indicated generally at 142) and past the dril bit 138, and is returned to the surface reservoir through the borehole 140 at the outside of the drill string 132. The drill string 132 is shown entering into a producible formation 144, having bored through earth formation 146.

The tool 130 is provided with four annular sonic transducers 150, 152, 154 and 156, each of which is of the magnetostrictive type. Magnetostrictive transducers are well known generally, so that design features are not described in detail herein. Transducers 150, 152, 154 and 156 are embedded within respective conformal annular channels in the tool 30, such that the exterior surface of the tool 130 is smooth and of constant cross section. Moreover, the tool 130 is extended longitudinally as far as practical toward the rotary bit 138, so as to preserve a constant cross section in the vicinity of the fluid analyzer elements. The length of the tool 130 in the uphole direction is not crucial if the constant cross section is readily maintained by the lower sections 134 and 136 of the drill string 132.

EVALUATION OF SENSOR PARAMETERS

A fluid analyzer of the FIG. 2 type can be viewed hypothetically as a system comprising a fluid filled tube in an infinite fluid. This type of system supports head-waves through the tube, as well as a number of higher order modes in addition to the Stoneley mode. All wave types but for the Stoneley mode are undesirable in the fluid analyzer of the present invention. The Stoneley wave can be identified and its velocity determined by either the techniques taught in the aforementioned Ingram patent or the aforementioned application of, or article by Kimball et al., using an appropriate multiple receiver array. Alternatively and preferably, parameter values are selected to avoid excitation and detection of most of the undesired modes.

The selection of values for the parameters of the fluid analyzer of FIG. 2 is made based on modeling the hypothetical system. To aid in the understanding and modeling of the hypothetical system for FIG. 2, refer to the theoretical study reported in the aforementioned article by van der Hijden et al., which is incorporated herein by reference. According to van der Hijden et al., a model for a fluid tube in an infinite fluid, the so called "inner problem," can be formulated as $P(z,t) = P_d + P_r$, where $P_d$ is direct arrival and $P_r$ is the reflected field. The direct arrival is the pressure field of a source in an infinite fluid. The expression for the reflected pressure field is given by:

$$P_r(z,t) = \frac{iP_0R_0}{4\pi} \int_{-\infty + i\omega''}^{\infty + i\omega''} d\omega X(\omega)e^{-i\omega t} \quad (1)$$

$$\int_{-\infty}^{\infty} dk_z A_1(k_z,\omega)e^{ik_z z}$$

where $P_0 R_0$ is a constant that is usually set to unity and $X(\omega)$ is the frequency spectrum of the source pulse. The frequency wavenumber function $A_1(k_z,\omega)$ is derived from the boundary conditions of the configuration. The modal contributions to the total solution in equation (1) correspond to simple poles in $k_z$ of $A_1$. If the denominator of $A_1$ is denoted by $D_1(\omega,k_z)$, then the dispersion relation for a particular mode $k_m(\omega)$ is given by:

$$D_1(\omega, k_z)|_{k_z=k_m(\omega)} = 0 \quad (2)$$

The inner problem was modeled by van der Hijden et al. with the following realistic parameter values:
Tube (steel) outer radius=3 inches
Tube (steel) thickness=0.4 inch
Tube (steel) compressional slowness=53 microseconds/foot
Tube (steel) shear slowness=98 microseconds/foot
Fluid slowness=190 microseconds/foot The inner problem was found to support a number of higher order modes, when provided with a source pulse having a center frequency of 10 kHz and 3 dB cutoffs at 6.1 and 13.9 kHz. Two types of modes other than the tube mode, which is dispersive but not attenuative, were found. The very highest modes are partially trapped fluid modes inside the tube, which are cut off at just above 15 kHz. The other modes are the extensional modes, which travel with a slowness of about 60 microseconds/foot, almost equal to the compressional velocity of the tube material. Generally, the extensional modes are seen to have a velocity closer to the extensional or bar velocity than to the steel compressional velocity. The extensional velocity $V_E$ is given by the square root of Young's modulus divided by the mass density of the steel.

The operation of the fluid analyzer of FIG. 2 is as follows. The tube or Stoneley wave velocity is readily measureable if excitation of the partly trapped modes is avoided. Hence, the upper bandwidth limit of the transmitted acoustic energy preferably does not exceed about 15 kHz, the cutoff frequency of the higher order modes, for a three inch tube. The operating characteristics of pulse generator 22 and transmitters $T_1$ and $T_2$ are established using methods well known in the art.

Notwithstanding the careful selection of operating frequency, the extensional modes remain. Yet, the extensional modes all have about the same arrival time, and are eliminated by gating, generally as follows. The velocity of the extensional modes is known, as explained above. The first extensional mode arrival reaches the receiver directly from the transmitter; hence, its arrival time is accurately known, as a function of the extensional velocity and distance of the receiver from the transmitter. In the apparatus of FIG. 1, controller 40 controls the timing of data acquisition by the receivers $R_1$ and $R_2$. At a time after the arrival of the primary extensional mode but before the earliest possible arrival of the Stoneley mode at the first receiver $R_1$ ($T_1$ being energized), amplifier 32 is gated ON, to pass the amplified signal detected by $R_1$. Similarly, at a time after the arrival of the primary extensional mode but before the earliest possible arrival of the Stoneley mode at the second receiver $R_2$ ($T_1$ being energized), amplifier 36 is gated ON, to pass the amplified signal detected by $R_2$. The amplifiers 32 and 36 simply are gated OFF before the arrival of any reflected extensional modes, although the ends of the tube 100 must be lengthened to delay the arrival of reflections from the end discontinuities.

Alternatively, the arrival times of the reflected extensional modes are determined as a function of the distances between the transmitters, tube ends, and receivers. The amplifiers are gated OFF during the time when an extensional mode arrival is expected, the duration of the latter being less than the duration of the Stoneley arrival.

A fluid analyzer of the FIG. 3 type can be viewed hypothetically in two parts: a first part comprising a fluid filled tube in an infinite fluid excited by a ring source in the infinite fluid; set within a second part comprising a fluid filled tube excited by a point source on the axis of the tube. The second part corresponds to the inner problem modeled by van der Hijden, although with different dimensions. The hypothetical first part of the FIG. 3 fluid analyzer also can be represented by the inner problem, the salient difference being that a point source within the tube gives rise to a fast extensional arrival that rings to the fluid arrival time, while a ring source outside of the tube gives rise to a much weaker fast extensional arrival with little ringing.

Both parts of the fluid analyzer of FIG. 3 support respective Stoneley and extensional wave arrivals. Nonetheless, the extensional and Stoneley of the first part, which are not of interest and would interfere with the Stoneley of interest, are extremely weak. Their effect can be eliminated by suitably setting the detection threshhold, if they are not already under the level of the lowest usable signal.

The hypothetical second part of the FIG. 3 embodiment, which is the dominant part of the system, is identical to the inner problem analyzed by van der Hijden, except for different dimensions. The effect of these dimensions is to decrease the frequency at which the higher order modes become problematic and limits the upper bandwidth of the source preferably to 12 kHz for a 4 inch radius pipe (e.g., casing).

A fluid analyzer of the FIG. 4 type can be hypothetically viewed as a first part comprising a fluid filled tube surrounded by an infinite fluid, excited by a ring source in the infinite fluid; set within a second part comprising a fluid filled borehole in an homogeneous solid, excited by a point source on the axis. The first part has been considered above, in the context of the FIG. 3 embodiment. The second part corresponds to the "outer problem" modeled by van der Hijden, which was found to give rise to the usual borehole arrivals: a compressional arrival, a shear arrival, modal arrivals, and a borehole Stoneley which is influenced by both the borehole fluid and formation. The compressional and shear arrivals generally precede the Stoneley and are gated out, generally as described above. The modes are more troublesome, however.

The selection of values for the parameters of the fluid analyzer of FIG. 4 is made based on modeling the second part, the dominant part of the hypothetical system for the FIG. 4 embodiment. van der Hijden et al. selected a borehole radius of 5 inches and a formation:fluid density ratio of 1.8. The troublesome borehole modes were found to be the completely trapped fluid modes that cut off at about 10 kHz for the exemplary dimensions; hence, the upper bandwidth limited is selected as 10 kHz for the FIG. 4 embodiment.

SINGLE PHASE FLOW ANALYZER

The fluid analyzers of the present invention are advantageous for measuring the velocity of a single phase fluid, such as a liquid. The measured Stoneley velocity "v" is influenced by the velocity of a flowing fluid, hence it differs from the velocity of the Stoneley wave $V_t$ in a still fluid. This measured, or apparent Stoneley velocity v is related to $V_t$ and the fluid velocity "V" as:

$$v_+ = V_t + V \quad (3)$$

$$v_- = V_t - V$$

depending on the relative directions of sound and fluid. The fluid velocity V can be obtained independent of the velocity $V_t$ if v is measured in opposite directions, as follows:

$$V = (v_+ - v_-)/2 \quad (4)$$

Numerous arrangements are capable of performing the measurement in opposite directions. One suitable arrangement comprises two transducers which operate first as a transmitter-receiver pair, then alternately as a receiver-transmitter pair. Another suitable arrangement places a transducer of one type between two transducers of the other type; for example, a transmitter located between two receivers. The preferred arrangement comprises two transmitters and two receivers, arranged as shown in FIGS. 1, 5, 6 and 7.

Figures 8, 9:
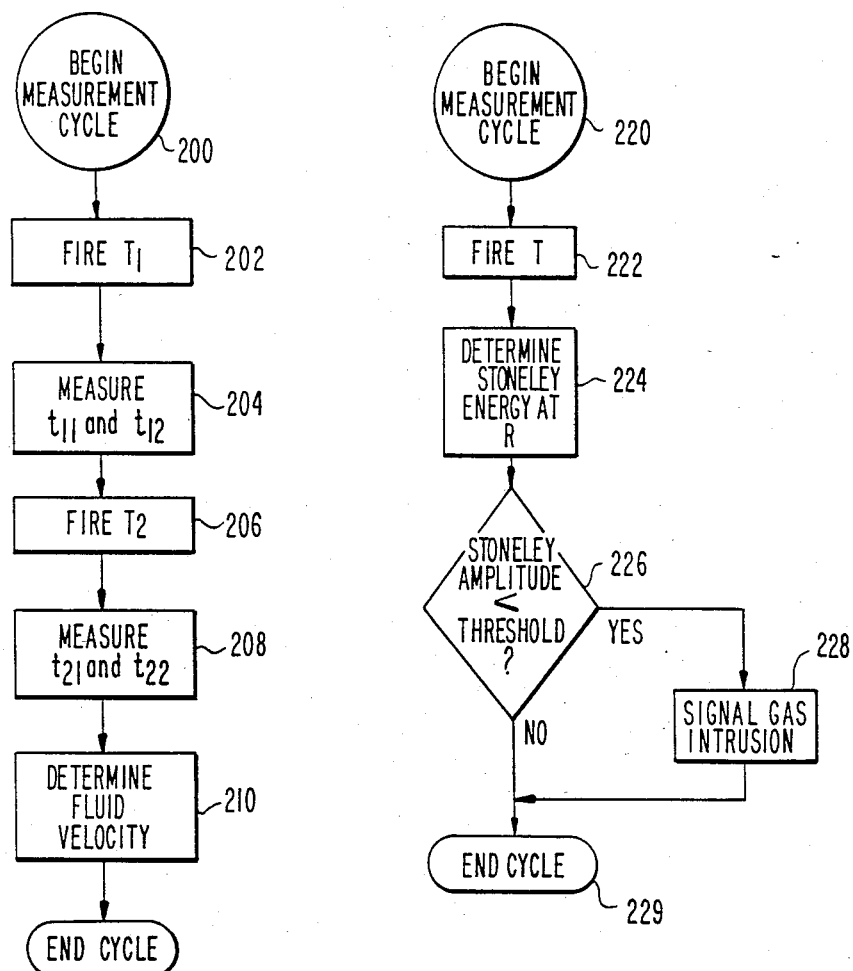
FIGS. 8 and 9 are flow diagrams, useful in explaining the operation of respective embodiments of the present invention.

The operation of the apparatus of FIG. 1 functioning as a single phase flowmeter is illustrated in FIG. 8. A measurement cycle is entered into at 200. Transmitter $T_1$ is fired at step 202. At step 204, amplifiers 32 and 36 are gated ON for the duration of an appropriate window, for detecting the Stoneley wave at $R_1$ and $R_2$ respectively. A first motion detection technique is used for measuring $t_{11}$, the travel time of the Stoneley wave between $T_1$ and $R_1$, and $t_{12}$, the travel time of the Stoneley wave between $T_1$ and $R_2$. Transmitter $T_2$ is fired next, as indicated at step 206. At step 208, amplifiers 36 and 32 are gated ON for the duration of an appropriate window, for detecting the Stoneley wave at $R_2$ and $R_1$ respectively. A first motion detection technique is used for measuring $t_{22}$, the travel time of the Stoneley wave between $T_2$ and $R_2$, and $t_{21}$, the travel time of the Stoneley wave between $T_2$ and $R_1$.

The fluid velocity V is determined at step 210, in accordance with the expression $$V = \tfrac{1}{2}\left(\frac{e}{t_1} - \frac{e}{t_2}\right) \quad (5)$$

where $$t_1 = t_{12} - t_{11} \quad (6);$$

and $$t_2 = t_{21} - t_{22} \quad (7)$$

and where "e" is the distance between $R_1$ and $R_2$.

DISPERSED PHASES FLUID ANALYZER

The fluid analyzers of the present invention are advantageous for measuring certain properties of dispersed phases, in addition to measurements of Stoneley velocity and fluid velocity discussed above. As used herein, the term "dispersed phases" refers to a flow wherein a gas phase is "finely" dispersed in a liquid phase. "Finely" means that the bubbles of a gas phase, for example, are much smaller than the diameter of the tubular conduit and the wavelength of the Stoneley mode.

The FIG. 7 embodiment is particularly advantageous for detecting gas entry into a well during measurement while drilling operations. For this application, the full transducer array shown is not necessary, and a single transmitter and a single receiver suffice. The operation of the FIG. 7 embodiment for this MWD embodiment is illustrated in FIG. 9, which shows a measurement cycle beginning at step 220. A transmitter, e.g. T, is fired at step 222, and the Stoneley energy is determined at step 224 by integrating the detected Stoneley mode over the detection window applied by controller 40 to a gated amplifier, e.g. amplifier 32 coupled to R. A comparison of the detected Stoneley energy with a threshhold value is made at step 226 to determine whether gas intrusion has occurred.

Figure 10:
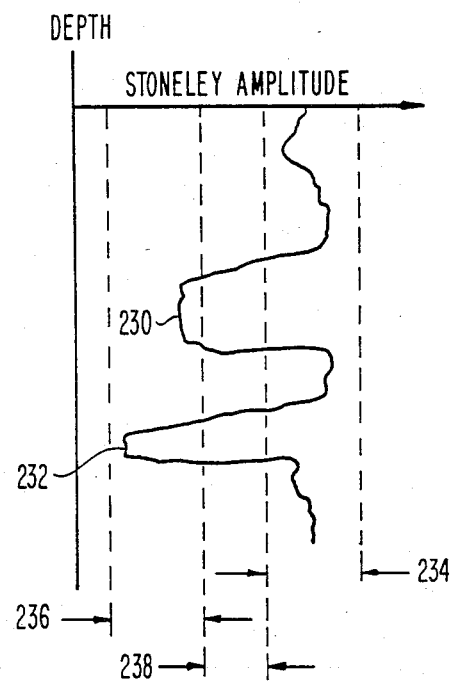
FIG. 10 is an illustrative well logging chart, useful in explaining the operation of an embodiment of the present invention.

The threshhold value which serves as the base for comparison in step 226 is obtained as follows. The Stoneley mode does not attenuate in a homogeneous material. Nonetheless, the Stoneley mode is extremely poorly coupled between a transducer and the fluid in a tubular conduit when the fluid is a liquid containing a gas phase, whether the gas is finely dispersed or dispersed in the form of bubbles or slugs. The poor coupling is evidenced by a dramatic drop in detected Stoneley energy, a much greater drop than would be caused by a change in the formation presently being traversed by the drill bit 138, for example. Two instances of gas intrusion are referenced by 230 and 232 in the illustrative well log of FIG. 10. In the case of a normal borehole mud and relatively unfractured formations, detected Stoneley energy can be expected to vary over a range generally indicated at 234. The variation may be due to one or more of several causes, such as differences in borehole diameter and in the permeability of the formation being investigated. When gas intrudes, the detected Stoneley energy drops dramatically, as apparent at 230 and 232, but also is influenced by the other factors and varies over a range indicated generally at 236. The threshhold value is set between the two ranges, as indicated generally at 238.

If the detected Stoneley energy falls below the threshhold value, an instance of gas intrusion is signaled at step 228 and the measurement cycle terminates at step 229. Otherwise, the measurement cycle simply terminates at step 229.

Figure 11:
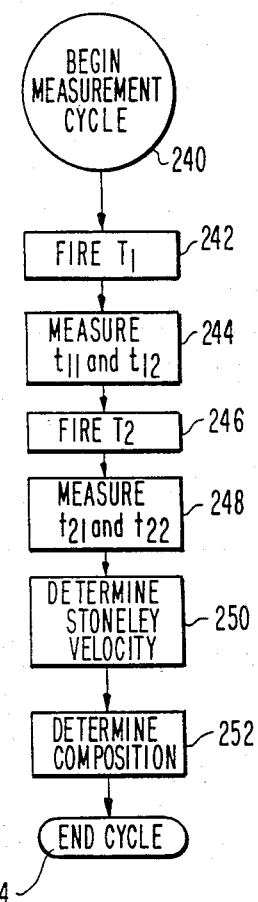
FIG. 11 is a flow diagram, useful in explaining the operation of an embodiment of the present invention.

The Stoneley mode also is advantageous for determining the relative composition of the dispersed phases, particularly in the embodiments of FIGS. 5 and 6. The operation of the fluid analyzer of the present invention for determining the composition of dispersed phases is illustrated in FIG. 11. The measurement cycle is entered into at 240. Transmitter $T_1$ is fired at step 242, and $t_{11}$ and $t_{12}$ are measured in step 244, substantially as explained above in the context of FIG. 8. Transmitter $T_2$ is fired at step 246, and $t_{22}$ and $t_{21}$ are measured in step 248, substantially as explained above in the context of FIG. 8.

The true or "still fluid" Stoneley velocity $V_t$ is obtained in step 252. The travel times obtained in steps 244 and 248 are combined to obtain the velocity $V_t$, in accordance with the expression $$V_t = (v_+ + v_-)/2 \tag{8}$$

derived from equation (3). The velocity $V_t$ is determined in accordance with the expression $$V_t = \tfrac{1}{2}\left(\frac{e}{t_1} + \frac{e}{t_2}\right) \tag{8a}$$

where $t_1 = t_{12} - t_{11}$ and $t_2 = t_{21} - t_{22}$ and
where "e" is the distance between $R_1$ and $R_2$.

The relative composition of the dispersed phases is obtained in step 252, essentially from data stored in the memory of analyzer 42. A relationship between the Stoneley velocity and various properties of gas and mud was reported in A. W. Wood, *A Textbook of Sound*, MacMillan and Company, New York, 1941. The relationship is $$V = \frac{\left(\dfrac{(1-\Phi)}{K_f} + \dfrac{\Phi}{K_g}\right)^{-\tfrac{1}{2}}}{((1-\Phi)\rho_f + \Phi\rho_g)^{\tfrac{1}{2}}} \tag{9}$$

where $\Phi$ is the porosity of the gas, $K_g$ is the bulk modulus of the gas, $K_f$ is the bulk modulus of the mud, $\rho_g$ is the density of the gas, and $\rho_f$ is the density of the mud. As representative values for these parameters are known, or alternatively can be independently measured, a curve of Stoneley velocity versus percentage composition of gas for the values is stored in the memory of analyzer 42. An illustrative curve 260 is provided in FIG. 12. The stored curve is consulted to obtain the relative composition. Alternatively, the expression may be stored and evaluated when supplied new values. The cycle ends at 254.

Figure 12:
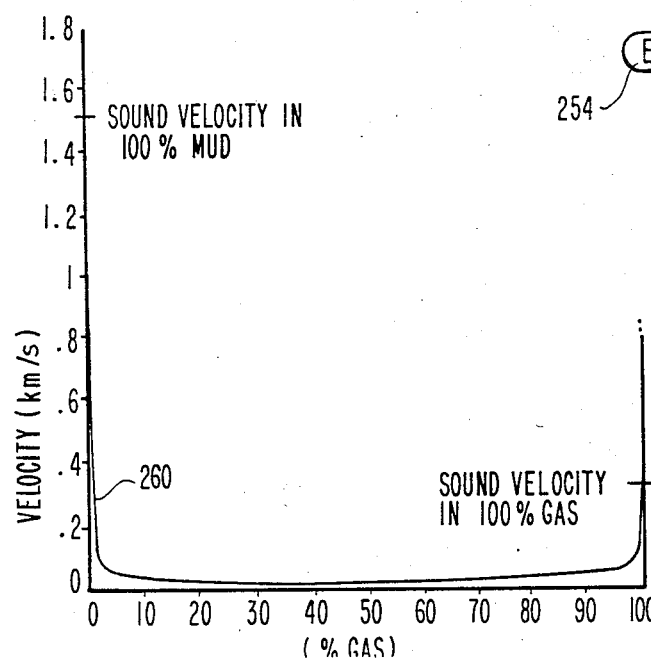
FIG. 12 is a graph of velocity versus porosity, which is useful in explaining the operation of an embodiment of the present invention.

As is apparent from FIG. 12, a high level of accuracy is required of the Stoneley velocity measurement if a meaningful determination of the volume of the gas phase is to be achieved. The bulk modulus of the gas and the density of the gas does not vary significantly, so that assumed values suffice. The mud bulk modulus and density do vary, however, and should be measured for best results. The measurement is obtained when gas is absent, as indicated by a high Stoneley velocity. In this instance, the Stoneley velocity is given by the square root of: the bulk modulus of the mud divided by the density of the mud. Stoneley velocity is determined as set forth above. The mud density is obtained by other means, such as, for example, described in U.S. Pat. No. 4,490,609, issued Dec. 25, 1984 to Chevalier. The mud bulk modulus is determined, and applied in equation (9) to determine gas volume by percentage when gas is present.

As also is apparent from FIG. 12, the Stoneley velocity alone also in indicative of gas intrusion. Stoneley velocity is generally high in the absence of gas, but drops abruptly when as little as two percent gas intrudes into the borehole fluid.

BUBBLE ANALYZER

The fluid analyzers of the present invention are advantageous for measuring the distribution of gas bubbles in a flowing liquid. As used herein, the term "bubble" refers to a gas phase of a fluid wherein the diameter of the bubble is about 1/100 the wavelength of the Stoneley mode.

A measurement of the bubble distribution is achieved by taking an attenuation spectrum over a range of Stoneley wavelengths. As noted above, one cause for a reduced measurement of Stoneley energy is weak coupling of the acoustic energy between a transducer and a fluid having a dispersed gas phase. Further reduction in measured Stoneley energy results from "resonance scattering," a phenomenon which is explained below with reference to a mathematical study by Sage, K. A. et al., Multipole Resonances in Sound Scattering from Gas Bubbles in a Liquid, *J. Acoust. Soc. Am.*, Vol. 65, No. 6, June 1979, pp. 1413–22. This further reduction is the basis for the attenuation spectrum.

The acoustic scattering properties of spherical gas bubbles in a liquid include the well-known "giant" monopole resonance at very low frequencies, which is due to the compressibility of the gas contained in the bubble. The giant monopole occurs at a frequency where the sonic wavelength is approximately 100 times larger than the bubble diameter. At resonance, the scattering cross section of the bubble is 10,000 times larger than the geometric cross section ($\pi r^2$) of the gas bubble. Other properties include a large number of higher frequency resonances which either are overtones of the monopole or correspond to both fundamental and overtones of bubble vibrations of higher multipolarity. These higher frequency resonances are much smaller in size than the giant monopole, however.

Figure 13:
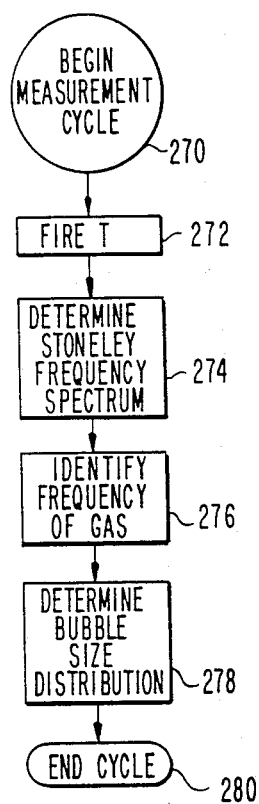
FIG. 13 is a flow diagram, useful in explaining the operation of an embodiment of the present invention.
Figure 14:
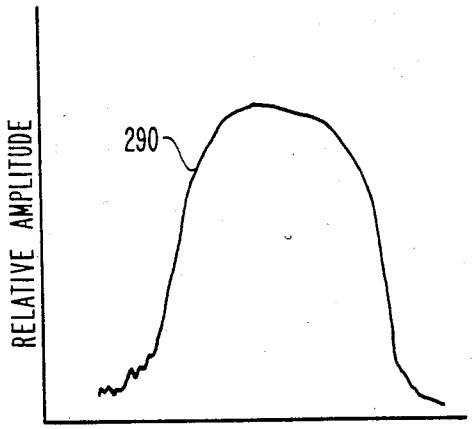
FIGS. 14 and 15 are graphs of respective frequency spectra of acoustic energy.

The operation of a bubble analyzer that uses the phenomenon of the giant monopole resonance is illustrated in FIG. 13. The measurement cycle is entered into at 270. The transmitter is fired at step 272. The transmitter characteristics are selected in accordance with the criteria set forth above. For example, given the embodiment of FIG. 5, the upper bandwidth is 15 kHz. In the absence of gas in the flowing fluid, the Stoneley frequency spectra associated with this source energy might appear as shown in the idealized curve 290 of FIG. 14.

Figure 15:
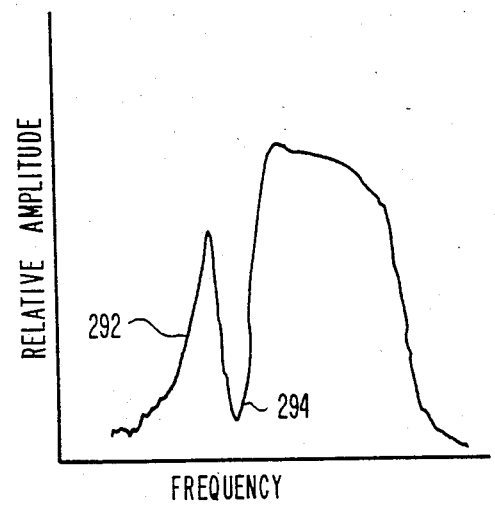

The Stoneley mode is detected and the Stoneley frequency spectrum determined at step 274. Standard techniques such as the fast Fourier transform are suitable for this purpose. An idealized Stoneley spectrum for the presence of bubbles in the flowing fluid is shown at 292 in FIG. 15. A relative amplitude scale is used as the y-axis in FIGS. 14 and 15, for convenience of comparison. The broad dip at 294 is attributable to a resonance at 1/100th of the diameter of the gas bubbles in the fluid present, indicating a concentration of gas bubbles of about the same diameter. The effect of the higher frequency resonances is very small. In any event, the higher frequency resonances occur outside of the bandpass applied by the filter 33 of FIG. 1.

The respective frequencies of dips are identified in step 276. A number of standard techniques are available for this purpose. One technique involves sliding a narrow bandpass window along the frequency spectrum 292, determining the energy in the window, and comparing the energy with neighboring determinations. A sharp drop in energy in a window indicates a dip, and the center frequency of the window is reported as the giant monopole resonance, from which the associated bubble size is determined in step 278 in accordance with the above-identified relationship. The bubble sizes determined in step 278 represent the bubble size distribution in the flowing fluid. The cycle ends at 280.

SLUG FLOWMETER

The fluid analyzers of the present invention are advantageous for measuring the velocity of slugs in a flowing liquid. As used herein, the term "slug" refers to a gas phase that occupies essentially the entire cross section of a tubular conduit.

Figure 16:
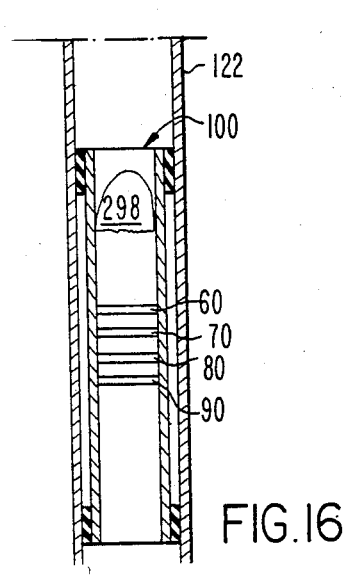
FIG. 16 is a cross sectional view of an embodiment of the present invention.

A measurement of slug velocity is achieved by detecting a backward traveling reflection of the Stoneley mode from the slug. The application is illustrated in FIG. 16, using the embodiment of FIG. 5 as an example. FIG. 16 shows the tool 100 within production casing 122. Transmitters 60 and 90 ($T_1$ and $T_2$ respectively), and receivers 70 and 80 ($R_1$ and $R_2$ respectively) are evident. A type of slug known as a Taylor bubble is illustrated generally at 298.

Figure 17:
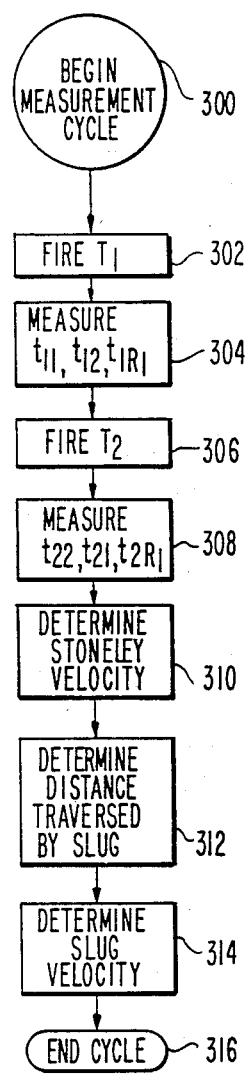
FIG. 17 is a flow diagram, useful in explaining the operation of an embodiment of the present invention.

The operation of a slug flowmeter using a pulse technique is illustrated in FIG. 17. The measurement cycle is entered into at 300. Transmitter $T_1$ is fired at step 302, and $t_{11}$, $t_{12}$, and $t_{1R1}$ are measured at step 304. The parameter $t_{1R1}$ is the time for the Stoneley mode to travel from $T_1$ to $R_1$, via the reflection path from the Taylor bubble 298. Transmitter $T_2$ is fired at step 306, and $t_{22}$, $t_{21}$ and $t_{2R1}$ are measured at step 308. The parameter $t_{2R1}$ is the time for the Stoneley mode to travel from $T_2$ to $R_1$, via the reflection path from the Taylor bubble 298.

The Stoneley velocity in a still fluid is determined at step 310, substantially as described for step 250 of FIG. 11.

Figure 18:
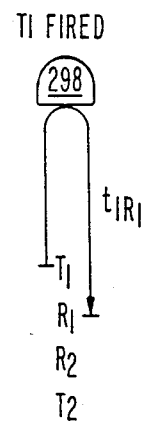
FIGS. 18 and 19 are sketches, useful in explaining the operation of an embodiment of the present invention.
Figure 19:
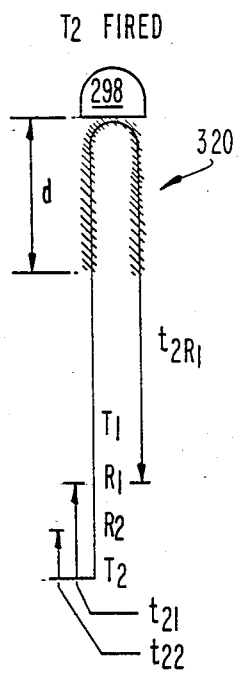

The distance, d, travelled by a slug in the time between firing of $T_1$ and $T_2$ is determined at step 312, by multiplying the Stoneley velocity determined in step 310 by half the travel time illustrated by the shaded line segment 320 in FIG. 19. The shaded line segment 320 is the difference between the time required for the Stoneley energy to travel from $T_1$ to $R_1$ via a reflection from the slug 298 at the time of firing of $T_1$, and the time required for the Stoneley energy to travel from $T_1$ to $R_1$ via a reflection from the slug 298 at the time of firing of $T_2$. In the notation of FIGS. 18 and 19, this relationship is expressed as:

$$d = \tfrac{1}{2}(V_t)(t_{2R1} - t_{21} - t_{22} - t_{1R1}) \tag{10}$$

where the term $(t_{2R1} - t_{21} - t_{22})$ is the time required for the Stoneley energy to travel from $T_1$ to $R_1$ via a reflection from the slug 298 at the time of firing of $T_2$, the distance between $T_2$ and $R_2$ being taken to be equal to the distance between $T_1$ and $R_1$.

If no slug is present in the fluid flowing through the tool 100, a reflection will occur at a known time due to the effective change in tube diameter at the upper end of the tool 100. Hence, a reflection detected at this known elapsed time indicates the absence of slugs in the fluid.

The slug velocity is determined at step 314 as the distance determined by expression (10) divided by the time between firing of $T_1$ and $T_2$. The cycle ends at 316.

While the present embodiments has been described with respect to several particular embodiments, it will be appreciated that the embodiments are illustrative only, in that the invention is not intended to be limited to the specifically described embodiments. Variations and combinations within the spirit and scope of the invention may occur to those skilled in the art. Accordingly, these variations are contemplated herein and are within the scope of the present invention.

I claim:

1. An apparatus for use in measuring a characteristic of a fluid that includes a liquid phase, contained in a tubular conduit, comprising:

means for exciting acoustic energy in said conduit, the frequency of excitation being selected to avoid significant excitation of higher order modes in said conduit section;

means for detecting acoustic energy excited in said tubular conduit, whereby a detection signal is provided;

means coupled to said detection means for compensating said detection signal for a fast arrival, whereby a compensated signal is provided;

means coupled to said compensating means for determining a property of said detected acoustic energy from said compensated signal; and means for determining a characteristic of said fluid from said property.

2. An apparatus as in claim 1, wherein said property is Stoneley velocity.

3. An apparatus as in claim 2, wherein said characteristic is fluid velocity.

4. An apparatus as in claim 2, wherein said characteristic is presence of gas.

5. An apparatus as in claim 2, wherein said characteristic is slug velocity.

6. An apparatus as in claim 1, wherein said property is Stoneley attenuation.

7. An apparatus as in claim 6, wherein said characteristic is presence of gas.

8. An apparatus as in claim 6, wherein said characteristic is size distribution of bubbles.

9. An apparatus for use in measuring a characteristic of a fluid that includes a liquid phase, contained in a tubular conduit, comprising:
means for exciting acoustic energy in said conduit;
means for detecting acoustic energy excited in said tubular conduit, whereby a detection signal is provided;
means coupled to said detection means for determining from said detection signal a property of Stoneley energy propagating in said tubular conduit; and
means for determining a characteristic of said fluid from said property.

10. An apparatus as in claim 9, wherein said property is Stoneley velocity.

11. An apparatus as in claim 10, wherein said characteristic is fluid velocity.

12. An apparatus as in claim 10, wherein said characteristic is presence of gas.

13. An apparatus as in claim 10, wherein said characteristic is slug velocity.

14. An apparatus as in claim 9, wherein said property is Stoneley attenuation.

15. An apparatus as in claim 14, wherein said characteristic is presence of gas.

16. An apparatus as in claim 14, wherein said characteristic is size distribution of bubbles.

17. An apparatus for use in measuring a characteristic of a fluid that includes a liquid phase, contained in a tubular conduit, comprising:
an elongated, generally tubular conduit section adapted for inclusion in said tubular conduit;
first and second acoustic transducers conformably mounted in said tubular section at a preselected axial distance from one another;
means coupled to said first transducer for exciting acoustic energy in said conduit section, the frequency of excitation being selected to avoid significant excitation of higher order modes in said conduit section;
means coupled to said second transducer for detecting acoustic energy excited in said tubular conduit, whereby a detection signal is provided;
means coupled to said detection means for compensating said detection signal for an extensional arrival, whereby a compensated signal is provided;
means coupled to said compensating means for determining an acoustic velocity from said compensated signal; and
means for determining a characteristic of said flowing fluid from said acoustic velocity.

18. An apparatus as in claim 17, wherein said first and second transducers are generally annular and operable in a radial vibration mode, said transducers being conformably mounted within an annular channel in the inside wall of said tubular section.

19. An apparatus for use in measuring a characteristic of a fluid that includes a liquid phase, contained in a well traversing earth formations, comprising:
an elongated tubular body;
first and second acoustic transducers conformably mounted on said tubular body at a preselected axial distance from one another;
means coupled to said first transducer for exciting acoustic energy in said well, the frequency of excitation being selected to avoid significant excitation of higher order modes in said well;
means coupled to said second transducer for detecting acoustic energy excited in said well, whereby a detection signal is provided;
means coupled to said detection means for compensating said detection signal for headwave arrivals, whereby a compensated signal is provided;
means coupled to said compensating means for determining an acoustic velocity from said compensated signal; and
means for determining a characteristic of said flowing fluid from said acoustic velocity.

20. An apparatus as in claim 19, wherein said first and second transducers are generally annular and operable in a radial vibration mode, said transducers being conformably mounted within an annular channel in the outside wall of said tubular section.

21. A method for measuring a characteristic of a fluid that includes a liquid phase, contained in a tubular conduit, comprising:
exciting acoustic energy in said conduit, the frequency of excitation being selected to avoid significant excitation of higher order modes in said conduit;
detecting acoustic energy excited in said conduit, whereby a detection signal is provided;
compensating said detection signal for a fast arrival, whereby a compensated signal is provided;
determining a property of said detected acoustic energy from said compensated signal; and
determining a characteristic of said flowing fluid from said acoustic velocity.

22. A method as in claim 21, wherein:
said fast arrival consists of extensional modes; and
said compensating step comprises the step of time filtering the components of said detection signal attributable to said extensional modes from said detection signal.

23. A method as in claim 21, wherein:
said fast arrival consists of compressional waves; and
said compensating step comprises the step of time filtering the components of said detection signal attributable to said compressional waves from said detection signal.

24. A method as in claim 21, wherein:
said fast arrival consists of compressional and shear waves; and
said compensating step comprises the step of time filtering the components of said detection signal attributable to said compressional and shear waves from said detection signal.

25. A method for measuring a characteristic of a fluid that includes a liquid phase, contained in a tubular conduit, comprising:
exciting acoustic energy in said conduit;

detecting acoustic energy excited in said conduit, whereby a detection signal is provided;
determining from said detection signal a property of Stoneley energy propagating in said tubular conduit; and
determining a characteristic of said fluid from said property.

26. A method as in claim 25, wherein said determining step comprises the steps of:
identifying a Stoneley arrival in said detection signal; and
determining an acoustic velocity in accordance with said identified Stoneley arrival.

* * * * *